United States Patent [19]

Supernaw et al.

[11] Patent Number: 4,939,362

[45] Date of Patent: Jul. 3, 1990

[54] BOREHOLE FLUID DENSITY WELL LOGGING MEANS AND METHOD

[75] Inventors: Irwin R. Supernaw; Jackie C. Sims, both of Houston, Tex.

[73] Assignee: Texaco Inc., White Plains, N.Y.

[21] Appl. No.: 276,734

[22] Filed: Nov. 28, 1988

[51] Int. Cl.[5] ............................................. G01V 5/12
[52] U.S. Cl. .................................. 250/269; 250/267; 250/268
[58] Field of Search ............ 250/269, 262, 268, 265, 250/253, 255, 256, 266, 267

[56] References Cited

U.S. PATENT DOCUMENTS

| | | | |
|---|---|---|---|
| 2,961,539 | 11/1960 | Egan | 250/269 |
| 3,662,172 | 5/1972 | Youmans | 250/268 |
| 4,423,323 | 12/1983 | Ellis et al. | 250/264 |
| 4,432,143 | 2/1984 | Moriarty | 250/268 |
| 4,490,609 | 12/1984 | Chevalier | 250/269 |
| 4,495,604 | 1/1985 | Dumanoir | 367/25 |
| 4,794,792 | 1/1989 | Flaum et al. | 73/152 |
| 4,810,876 | 3/1989 | Wraight et al. | 250/256 |

*Primary Examiner*—Constantine Hannaher
*Assistant Examiner*—Edward J. Glick
*Attorney, Agent, or Firm*—Robert A. Kulason; James J. O'Loughlin; Ronald G. Gillespie

[57] ABSTRACT

The present invention is a density meter which includes a well logging sonde that is inserted into a borehole traversing an earthen formation. The sonde includes within it a source which emits gamma rays into the borehole fluid and a detector assembly which detects gamma rays from the borehole fluid and provides a count signal corresponding to a count of the detected gamma rays. A caliper is also located in the sonde and it continually measures the diameter of the borehole as the sonde moves through the borehole and provides a caliper signal corresponding to the diameter measurement. A cable connected to the detector assembly and to the caliper conveys the count signal and a caliper signal to the surface where surface electronics includes apparatus which processes the count signal and the caliper signal to provide a signal corresponding to the density of the fluid in the borehole.

6 Claims, 1 Drawing Sheet

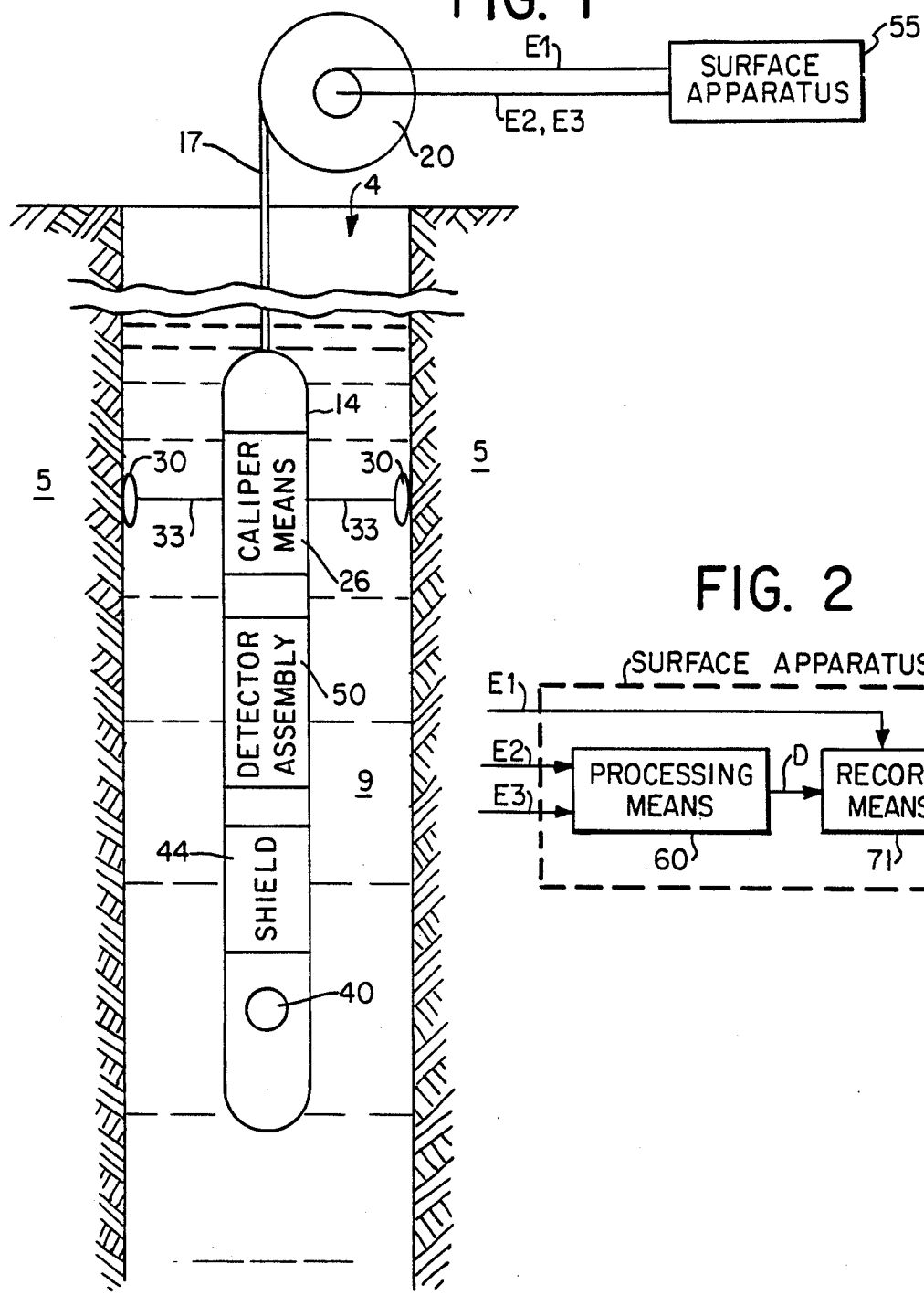

BOREHOLE FLUID DENSITY WELL LOGGING MEANS AND METHOD

BACKGROUND OF THE INVENTION

Field of the Invention

The present invention relates to well logging means and methods in general and, more particularly, to a well logging means and method for determining the density of a fluid in the borehole.

SUMMARY OF THE INVENTION

The present invention is a density meter which includes a well logging sonde that is inserted into a borehole traversing an earthen formation. The sonde includes within it a source which emits gamma rays into the borehole fluid and a detector assembly which detects gamma rays from the borehole fluid and provides a count signal corresponding to a count of the detected gamma rays. A caliper is also located in the sonde and it continually measures the diameter of the borehole as the sonde moves through the borehole and provides a caliper signal corresponding to the diameter measurement. A cable connected to the detector assembly and to the caliper conveys the count signal and a caliper signal to the surface where surface electronics includes apparatus which processes the count signal and the caliper signal to provide a signal corresponding to the density of the fluid in the borehole.

The objects and advantages of the invention will appear more fully hereinafter from a consideration of the detailed description which follows, taken together with the accompanying drawing, wherein one embodiment of the invention is illustrated by way of example. It is to be expressly understood, however, that the drawing is for illustration purposes only and is not to be construed as defining the limits of the invention.

DESCRIPTION OF THE DRAWINGS

FIG. 1 is a diagrammatic representation of a well logging system constructed in accordance with the present invention which measures the density of fluid in the borehole.

FIG. 2 is a simplified block diagram of the surface apparatus shown in FIG. 1.

DESCRIPTION OF THE INVENTION

In production logging, a common procedure is the measurement of the profile of the oil and water flow rates at depth in the well. These rates are estimated from the determinations of water holdup and total flow rate. The estimate of the water holdup is in turn derived from an assessment of the density of the fluid in the borehole. Therefore, the determination of the average density of the borehole fluid greatly affects the accuracy of results of the water flow calculation.

There is evidence which indicates that at least in large diameter boreholes in regions where oil is entering the borehole where water is flowing, there exists a density gradient across the borehole with the lighter (oil rich) portion near the formation wall and the heavier (water rich) fraction in the center. This situation presents a problem because all the tools used to make the density determination in production logging do so with a small tool (1 11/16 inch diameter) centralized in the borehole. Whether these tools measure the density by gamma ray attenuation of a well collimated source or by pressure differential (the two commonly employed methods), they will suffer the limitation that they do not sense the true average density of the fluid in question but give a high estimation thereof. This becomes a severe problem in large boreholes (6-7 inch diameter).

With reference to FIG. 1, there is a borehole 4 traversing earthen formation 5 which is partially filled with a still or flowing fluid 9 combination of oil and water in various concentrations. A sonde 14 is inserted into the fluid 9 with a conventional logging cable 17 from a shreave wheel 20. Shreave wheel 20 provides a signal E1 corresponding to the depth of sonde 14 into borehole 4.

Sonde 14 includes conventional type caliper means 26 which urges pads 30 against the wall of borehole 4 by means of arms 33. Caliper means 26 provides a signal E2 related to the diameter of the borehole.

Sonde 14 includes a nuclear source 40 which emits gamma radiation. Nuclear source 40 may be $137_{CS}$. The gamma radiation, since it is un-collimated will radiate the radiation in all directions. However, within sonde 9 is a shield 44 which prevents the radiation from traveling inside of sonde 14.

Beyond shield 44 in sonde 14 is a detector assembly 50 which is a conventional type gamma ray detector assembly and as such would include a scintillation crystal which provides a light pulse in accordance with detector gamma radiation. The light pulses are converted to electrical pulses by photomultiplier tubes, and so forth. All of the material within detector assembly 50 is standard and well known in the art. Suffice to say that detector assembly 50 provides a signal E3 corresponding to a count rate of the detected gamma rays.

As noted before, shield 44 absorbs the emitted gamma rays within sonde 14, but other gamma rays emitted by source 40 escape into the fluid and undergo compton scattering in the fluid and formation and find their way to detector assembly 50. Thus any gamma entering detector assembly 50 has passed through a path length of the fluid which will allow it to be influenced by the total mass n the borehole.

It follows that knowing the proximity of the formation from the signal provided by the caliper means 26 that the affect of the observed count rate is related to the average density of the fluid in borehole 4, since a denser fluid would absorb a greater fraction of the scattered protons. Detector assembly 50 may include a counter itself or it could provide the pulses from the photomultiplier tube uphole directly where as noted along with the signal from caliper means 26 can be used to determine the density.

The signals E2 and E3 are provided by way of a conventional type well logging cable 17 to surface apparatus shown in FIG. 2.

It would be obvious to one skilled in the art that the necessary detailed elements for applying signals to well logging cables are well known in the art and adds nothing to the disclosure of the present invention to discuss them at this time. Similarly, with the pick-off circuits that are known in the art for picking off the signals from cable 17 and providing them to elements of surface apparatus. Surface apparatus 55 includes processing means 60 receiving signal E1 from the shreave wheel and signals E2 and E3 from cable means 17 determines the density of the fluid and relates it to the length in the borehole.

Process means 60 determines the density $\rho$ of the borehole fluid in accordance with the following equation $$\rho = f_{cr}(CR - CR_B) - f_{cal}(CAL.)$$

where $f_{cr}$ represents function of a count rate, CR is the count rate of the detected gamma rays, $CR_B$ is the background count rate of background gamma rays and $f_{cal}$ represents a function of caliper signal CAL. The background count rate $CR_B$ is determined by a separate run without energization.

Process means 60 provides an average density signal to record means 71. Record means 71 also receives signal E1 which drives record means 71 so that the density signal is correlated to depth in the borehole.

What is claimed is:

1. A well logging system which measures the density of a fluid in a borehole traversing an earthen formation, comprising:
    sonde means including:
    source means for emitting gamma rays into the borehole fluid,
    detector means for detecting gamma rays from the borehole fluid and providing a count rate signal corresponding to a count rate of the detected gamma rays, and
    caliper means for continually measuring the diameter of the borehole and providing a caliper signal corresponding thereto;
    cable means connected to the detector means and to the caliper means for conveying the count rate signal and the caliper signal to the surface, and
    surface electronics including:
    processing means connected to the cable means for processing the count rate signal and the caliper signal to provide a density signal corresponding to the density of the fluid in the borehole.

2. A system as described in claim 1 in which the surface electronics further comprises:
    means cooperating with the cable means for providing a signal corresponding to the depth of the sonde means in the borehole, and
    means connected to last mentioned means and to the processing means for recording the density signal in correlation to the depth of the sonde means.

3. A system as described in claim 2 in which the processing means includes:
    means for providing the density signal in accordance with the caliper signal, the count rate signal and the following equation $$\rho = f_{cr}(R - R_B) - f_{cal}(CAL.)$$

where $\rho$ is the density of the fluid, $f_{cr}$ represents a function of a count rate, CR is the count rate of the detected gamma rays, $CR_B$ is a count rate of background gamma rays, $f_{cal}$ represents a function of a caliper signal CAL.

4. A well logging method which measures the density of a fluid in a borehole traversing an earthen formation, comprising:
    emitting gamma rays into the borehole fluid from a source located in a well logging sonde,
    detecting gamma rays from the borehole fluid with a detector located in the well logging sonde,
    providing a count rate signal corresponding to a count rate of the detected gamma rays,
    continually measuring the diameter of the borehole,
    providing a caliper signal corresponding thereto to the measured borehole diameter,
    conveying the count rate signal and the caliper signal to the surface with a cable, and
    processing the count rate signal and the caliper signal at the surface to provide a density signal corresponding to the density of the fluid in the borehole.

5. A method as described in claim 4 further comprising the steps of:
    providing a signal corresponding to the depth of the sonde in the borehole, and
    recording the density signal in correlation to the depth of the sonde.

6. A method as described in claim 5 in which the processing step includes:
    providing the density signal in accordance with the caliper signal, the count rate signal and the following equation $$\rho = f_{cr}(R - R_B) - f_{cal}(CAL.)$$

where $\rho$ is the density of the fluid, $f_{cr}$ represents a function of a count rate, CR is the count rate of the detected gamma rays, $CR_B$ is a count rate of background gamma rays, $f_{cal}$ represents a function of a caliper signal CAL.

* * * * *